United States Patent [19]
Riley, II

[11] Patent Number: 4,799,497
[45] Date of Patent: Jan. 24, 1989

[54] APPARATUS FOR MEASURING KNEE LAXITY

[76] Inventor: James W. Riley, II, 404 S. Main, Eureka, Ill. 61530

[21] Appl. No.: 570,864

[22] Filed: Jan. 16, 1984

[51] Int. Cl.$^4$ ............................................. A61B 5/00
[52] U.S. Cl. .................................... 128/774; 128/782
[58] Field of Search ............... 128/774, 782; 33/174 P

[56] References Cited

U.S. PATENT DOCUMENTS

| | | | |
|---|---|---|---|
| 4,277,828 | 7/1981 | Tateishi | 128/774 X |
| 4,323,080 | 4/1982 | Melhart | 128/774 |

FOREIGN PATENT DOCUMENTS

| | | | |
|---|---|---|---|
| 2638169 | 2/1978 | Fed. Rep. of Germany | 128/774 |
| 103619 | 6/1983 | Japan | 128/774 |
| 1041091 | 9/1983 | U.S.S.R. | 128/774 |

OTHER PUBLICATIONS

Bechtel et al., "Skier's Knee", Physic. & Sports Medicine, vol. 12, No. 11, 11/84, pp. 51-54.

Primary Examiner—Edward M. Coven
Attorney, Agent, or Firm—Laney, Dougherty, Hessin & Beavers

[57] ABSTRACT

An apparatus for measuring a person's knee laxity. A pair of clamps are provided to secure a person's knee adjacent one end of a table. A hinged platform is pivotally attached to the table end. The person's ankle is clamped to a smaller platform which is supported by rollers on the hinged platform. An elongate tibia-tracking element has one end pivotally connected to the hinged platform beneath the knee and the other end connected to the ankle-supporting platform. A potentiometer is connected to the tibia tracking element and provides resistance readings which are proportional to angular movement of the element. An ohmeter senses resistance while force is applied to the medial or lateral sides of the tibia. Correlation of the applied forces to the degree of tibia movement for each force provides an indication of knee laxity.

10 Claims, 2 Drawing Sheets

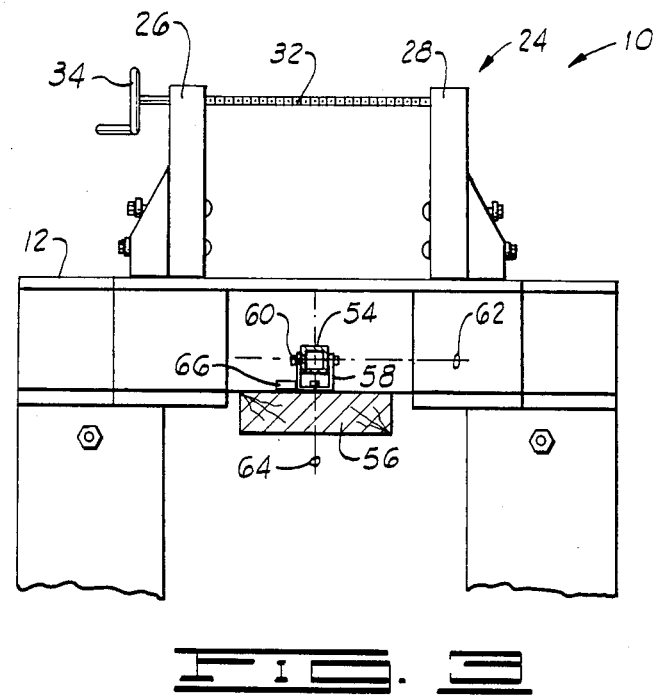
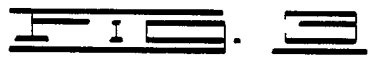
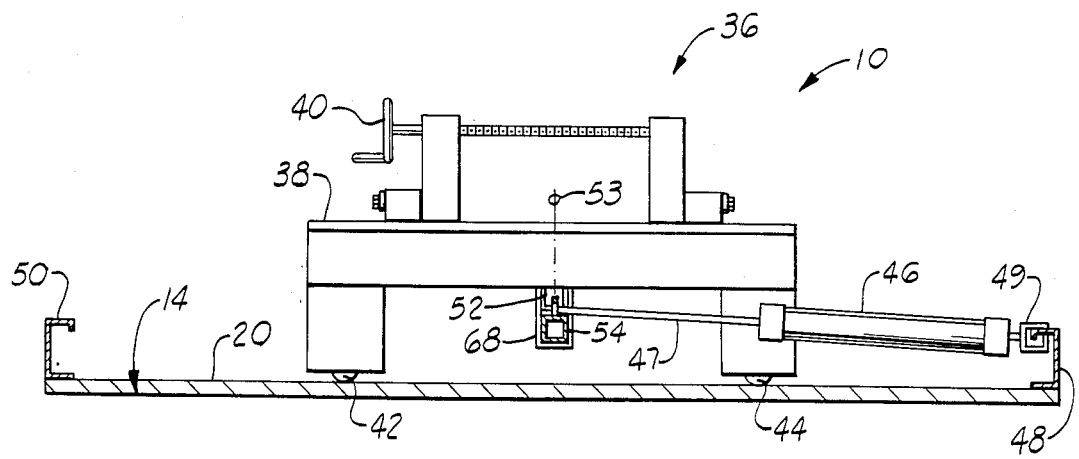
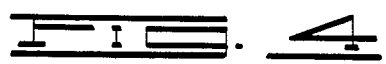

APPARATUS FOR MEASURING KNEE LAXITY

BACKGROUND AND SUMMARY OF THE INVENTION

The instant invention pertains to methods and apparatus for measuring a person's knee laxity.

Human knee joints may range from being very tight to being very loose. Generally, whether a knee joint is tight or loose depends upon the qualities of the cartilidge in the knee joint as well as on the muscles which support the joint. Knee joints which are either very loose or very tight are subject to injury. If the laxity of the knee joint is known and if it is considered to be too tight or too loose, appropriate treatment may be administered to remedy or at least reduce the severity of the condition. It is therefore desirable to be able to quantify the laxity of human knee joints.

The instant apparatus includes means for fixing a person's knee. Also included is means for selectively applying force against the lateral (outside) or against the medial (inside) portion of the tibia. When the force is so applied, measuring means measure the amount of tibia movement. The correlation of tibia movement with the amount of force required to generate such movement provides an indication of knee laxity. The application of force and movement measurement may be made at varying degrees of knee flexion.

It is therefore a general object of the instant invention to provide an indication of knee laxity by correlating the amount of tibia movement with the amount of force necessary to generate such movement.

It is a more specific object of the instant invention to provide such an indication with force being applied to the tibia in a plane substantially parallel to the medial-lateral plane.

These and other objects and advantages of the instant invention will become more fully apparant when the following detailed description is read in view of accompanying drawings, wherein:

FIG. 4 is a view taken along line 4—4 in FIG. 1; and

FIG. 5 is a schematic diagram of a portion of the instant embodiment of the invention.

DETAILED DESCRIPTION OF THE PREFERRED EMBODIMENT OF THE INVENTION

Figure 1:
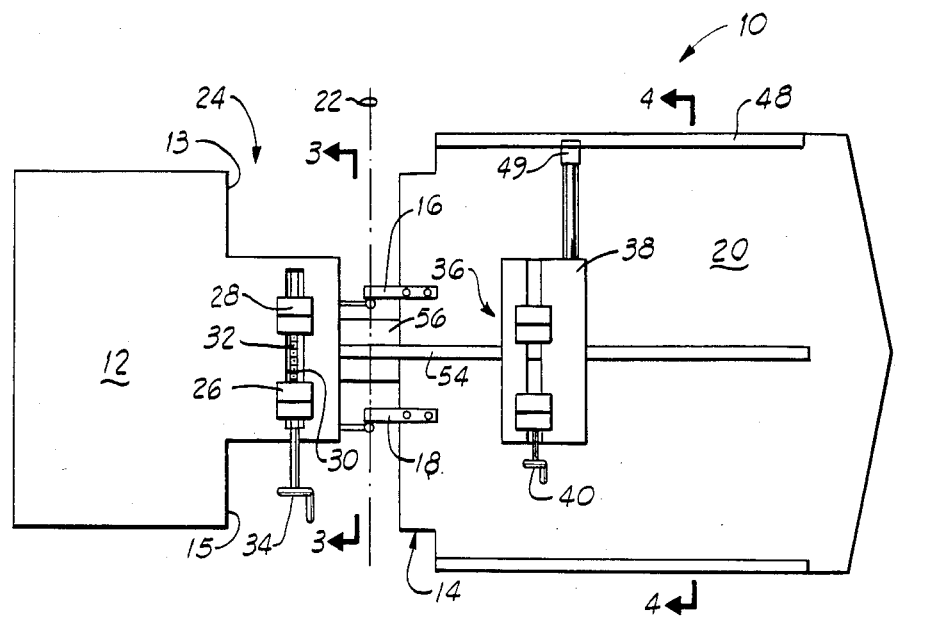
FIG. 1 is a top plan view of the preferred embodiment of the invention.
Figure 2:
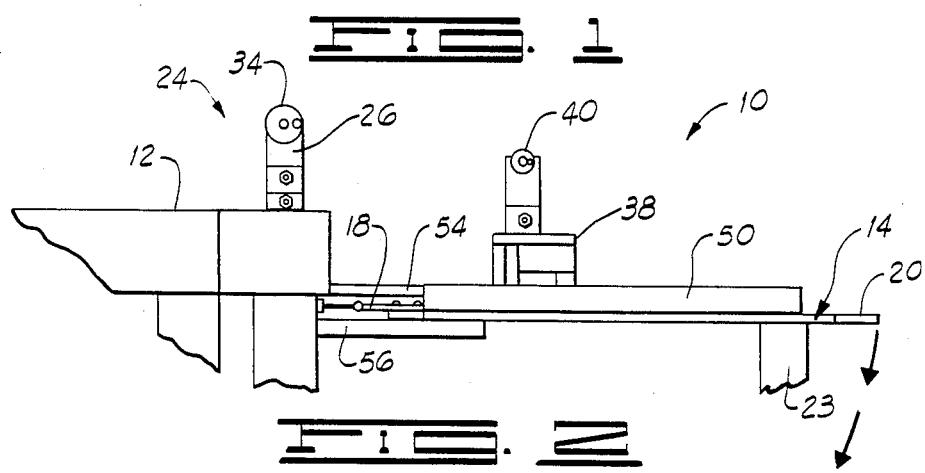
FIG. 2 is a side view of the embodiment of FIG. 1.

Turning attention to the drawings, indicated generally at 10 is a knee laxity testing device constructed in accordance with the instant invention. Device 10 includes a platform or table 12 for supporting a person. The table includes a pair of forword edges 13, 15. A substantially planar element or hinged platform 14 is connected to table 12 for hinging movement relative thereto via hinges 16, 18. Hinged platform 14 is also referred to herein as a base. Platform 14 includes an upwardly directed support surface 20. Hinges 16, 18 enable pivotally downward movement of platform 14 as indicated by the arrows at the right most end of the platform. The movement is about the pivotal axis of hinges 16, 18 as indicated by the dot-dash line 22 in FIG. 1. Platform 14 may be fixed at a selected degree of angulation by adjusting the height of a platform support 23 positioned beneath the platform.

Mounted on one end of table 12 is a clamp, indicated generally at 24, such also being referred to herein as a knee immobilizer or as knee fixing means. Clamp 24 includes a pair of upright clamp members 26, 28, the lower end of each being received in a slot 30 formed in the top of table 12. Each of clamp members 26, 28 are maintained within slot 30 by structure (not visible) mounted on the lower end of each of the clamp members beneath the top of table 12. Each of the clamp members is slidable along the length of the slot. A threaded rod 32 is threadibly received within bores (not visible) formed in the upper ends of members 26, 28. Clockwise rotation of rod 32 via a handle 34 mounted on one end thereof, draws clamp members 26, 28 together, and when a knee is received therein, fixes the position of the knee. Likewise, counterclockwise rotation of the rod moves clamp members 26, 28 away from one another.

A clamp, indicated generally at 36 (which is similar to clamp 34) is mounted on a platform 38. Clamp 36 is also referred to herein as an ankle immobilizer or as ankle fixing means. Clamp 36, like clamp 34 includes a pair of upright members, a threaded rod therebetween and a control handle 40 for rotating the rod which draws the clamp members together or spreads them apart dependant upon the direction of rotation.

Platform 38 is supported on platform 14 via rollers 42, 44, such being mounted on axles (not shown) which are secured to the underside of the platform to enable lateral rolling movement, as viewed in FIG. 4, of the platform. A pneumatic ram 46 includes the usual rod 47. One end of ram 46 is mounted on a C-beam 48 which is fixedly secured along one side of platform 14. The ram is connected to the C-beam via a detachable connector 49. A second C-beam 50 is fixedly secured along the other side of the platform opposite C-beam 48. Rod 47 is pivotally connected to the underside of platform 38 via a caster 52. The caster is rotatable about a vertical axis therethrough, such being indicated by dot-dash line 53. Ram 46 is referred to herein as means for moving the ankle supporting means.

A tibia-tracking element 54, also referred to herein as pivotally connecting means, has one end connected to board 56. Board 56 is fixedly attached to the underside of platform 14 and extends from the platform under table 12 beneath clamp 24. Element 54 is connected to board 56 via a caster 58. The element is bolted by a bolt 60 to the caster which in turn is connected to board 56. Element 54 is rotatable both about the axis of the bolt, indicated by dot-dash line 62 and the axis of rotation of caster 58, indicated by dot-dash line 64. Axis 64 is centered beneath clamp members 26, 30 so that it passes through the joint of a knee secured by clamp 24.

A potentiometer 66 is mounted on board 56 to the rear (as viewed in FIG. 3) of caster 58. In the instant embodiment of the invention, the potentiometer is a Slide-Trol sliding 5 kilohm potentiometer. The slide of the potentiometer (not visible) is connected to element 54 and is moved proportionate to movement of the element about axis 64.

Element 54 is received within a u-clamp 68 which is mounted on the underside of platform 38. The element is fixedly clamped to the underside of the platform via the u-clamp; however, the position along the element at which the clamp, and therefor platform 38, is attached may be easily varied.

Turning now to FIG. 5, parts which have previously been described in other figures are designated by the same numbers in FIG. 5. An ohmeter 70 is connected to potentiometer 66 and measures variations in its resistance. The ohmeter is connected as shown to input terminals of a computer 72. A conventional keyboard 73 is connected to the computer for programming it and for providing command signals to the computer. A conventional pressure transducer 74 is mounted on ram 46 and generates an electrical signal proportional to the air pressure in ram 46. The air pressure in the ram is proportional to the force applied by the ram along the axis of rod 47. The signal so generated is appiied to an input terminal of computer 72. Conductor 76 is connected to an output terminal of the computer and to a conventional valve 77 which opens and closes responsive to signals on conductor 76. A compressed air source 78 is connected to the valve input while the output is connected to ram 46. Thus, when valve 77 is opened responsive to signals on conductor 76, the compressed air is supplied to the ram. An output device 80, e.g., a printer is connected to computer 72 to display output information generated by a program in the computer which operates upon the data supplied by ohmeter 70 and by transducer 74. The program is designed to display the relationship between the degree of tibia movement and the force applied by the ram. A person having ordinary skill in the art of computer programming can easily program the computer to display such an output.

In operation, when it is desired to measure the laxity of a person's knee, the person sits on table 12 and places, e.g., his right knee between clamp members 26, 28. The person's left knee is bent with the left leg extending downwardly from the table just forward of edge 13. If the laxity of the left knee is to be measured, the left knee is placed between the clamp members while the right leg extends downwardly forward of edge 15. Since, for the purposes of this example, the right knee is being measured, the right ankle is placed between the clamp members of clamp 36 on platform 38. Dependent upon the length of the person's tibia, it may be necessary to loosen u-clamp 68 and adjust the position of platform 38 along element 54 so that when the perons's knee is clamped in clamp 24, the ankle will fall between the clamp elements of clamp 36. Also, if necessary, connector 49 may be disconnected from C-beam 48 and re-connected so that the axis of ram 46 forms a substantially ninety degree angle with respect to the axis of element 54. Next, the degree of knee flexion at which laxity is to be tested is determined and platform support 23 is lowered, if necessary, to permit downward rotation of platform 14 about axis 22. Suport 23 is set to support platform 14 so that the desired angulation of the platform is obtained.

Once the knee and ankle are clamped and the degree of angulation of platform 14 is selected, a command may be given to computer 72 via keyboard 73. The command causes the computer to generate a signal which is applied to line 76 which causes opening of valve 77. As the valve opens, pressurized air enters ram 46 thus causing extension of rod 47 and leftward movement (in FIG. 4) of platform 38 on rollers 42, 44. Such movement applies a force directed toward the lateral side of the tibia via the ankle. Transducer 74 generates a signal proportional to air pressure in ram 46 and provides the signal to the computer. As air pressure increases, force exerted by the ram against the platform increases as does tibia movement.

Figure 3:
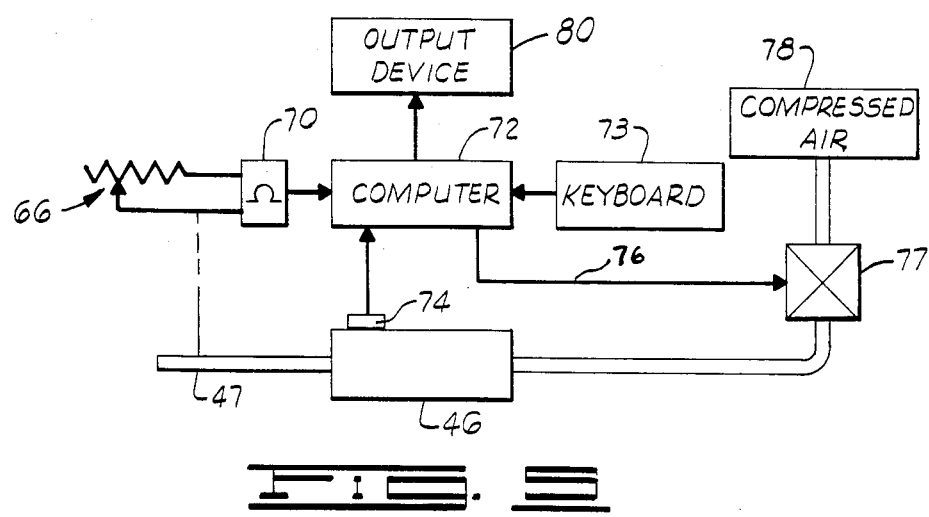
FIG. 3 is a view taken generally along line 3—3 in FIG. 1.

Since element 54 is clamped to the underside of the platform, lateral movement of the platform causes rotation of the element about axis 64 (in FIG. 3). As will be recalled, such rotation changes the resistance of potentiometer 66 proportional thereto. Ohmeter 70 detects variations in the resistance of potentiometer 66 and generates a signal proportional to such variations which is provided to computer 72. The computer is programmed to correlate the signals provided from ohmeter 70 and from transducer 74 and to generate a graph of tibia movement relative to force applied, such providing to output device 80 for display, e.g., on a monitor or for printing.

When it is desired to test the laxity of the right knee by applying force to the medial side of the tibia, via the ankle, connector 49 is disconnected from C-beam 48 and ram 46 is pivoted one hundred eighty degrees about axis 53 so that connector 49 is adjacent C-beam 50. The connector is then attached to C-beam 50 in the same manner in which it was attached to beam C-beam 49. The above-described procedure for generating pressure in the ram and for generating a graph which is indicative of knee laxity is repeated with the force this time being applied from the medial side of the tibia. The mediallateral plane referred to herein is the plane substantailly parallel to platform 14.

It is to be appreciated that variations and modifications of the foregoing described embodiment may be made without parting from the spirit of the invention which is defined in the following claims.

I claim:

1. Am apparatus for measuring knee laxity of a person comprising:
    means for fixing a person's knee;
    means for applying a force against the person's tibia along an axis substantially parallel to the lateral-medial plane of the tibia, said means for applying force against the person's tibia including:
        a support surface,
        means for supporting the person's ankle, said supporting means being rollingly mounted on said support surface, and
        means for moving said supporting means relative to said surface; and
    means for measuring the angular deflection of the tibia when such a force is applied thereto.

2. The apparatus of claim 1 wherein said supporting means includes a platform having rollers mounted on the underside thereof.

3. The apparatus of claim 1 wherein said supporting means includes means for fixing the person's ankle mounted thereon.

4. The apparatus of claim 3 wherein said means for fixing the person's knee and ankle each comprise a clamp.

5. The apparatus of claim 1 wherein said means for measuring the angular deflection of the tibia comprises:
    a base;
    means for pivotally connecting said ankle supporting means to said base; and
    means for detecting the angular movement of said connection means.

6. The apparatus of claim 5 wherein said base is said support surface.

7. The apparatus of claim 5 wherein said detecting means comprises:

a potentiometer having a control for varying the resistance thereof;

means for connecting said potentiometer control to said pivotally connected means; and means for measuring said potentiometer resistance, said measuring means being operably attached to said potentiometer.

8. An apparatus for measuring a person's knee laxity comprising:

a platform for supporting the person, said platform having a substantially planar element;

a knee immobilizer mounted on said platform adjacent one end thereof, said knee immobilizer being hingingly connected to said substantially planar element;

an ankle immobilizer having rollers mounted thereon for rolling on said substantially planar element;

an elongate tibia-tracking element having a first end pivotally connected to said platform and a second end pivotally connected to said ankle immobilizer, said tibia-tracking element being substantially parallel to a person's tibia when the person's knee is received in said ankle immobilizer;

means for measuring angular movement of said tibia-tracking element; and means for applying a force against a person's tibia along an axis substantially parallel to the lateral-medial plane of the tibia.

9. The apparatus of claim 8 wherein said force applying means comprises a ram having a first end connected to said ankle immobilizer and a second end connected to one side of said planar element.

10. The apparatus of claim 9 wherein said apparatus further includes means for connecting the second end of said ram to the other side of said planar element.

* * * * *